US006692481B2

(12) United States Patent  
Guerrero (10) Patent No.: US 6,692,481 B2
(45) Date of Patent: Feb. 17, 2004

(54) METHOD AND APPARATUS FOR TREATMENT OF AMBLYOPIA

(76) Inventor: John M. Guerrero, 3781 SW. Coquina Cove Way, Apt. 203, Palm City, FL (US) 34990

( * ) Notice: Subject to any disclaimer, the term of this patent is extended or adjusted under 35 U.S.C. 154(b) by 0 days.

(21) Appl. No.: 10/186,062

(22) Filed: Jun. 28, 2002

(65) Prior Publication Data

US 2003/0114830 A1 Jun. 19, 2003

Related U.S. Application Data

(60) Provisional application No. 60/340,301, filed on Dec. 13, 2001.

(51) Int. Cl.$^7$ .............................................. A61M 31/00
(52) U.S. Cl. ...................................... 604/521; 604/294
(58) Field of Search ......................... 604/890.1, 891.1, 604/500, 521, 294; 351/203, 222; 514/220, 912, 724

(56) References Cited

U.S. PATENT DOCUMENTS

| | | | |
|---|---|---|---|
| 4,474,751 A | 10/1984 | Haslam et al. | |
| 4,784,157 A | 11/1988 | Halls et al. | |
| 5,618,274 A | 4/1997 | Rosenthal | |
| 6,511,175 B2 * | 1/2003 | Hay et al. | ..................... 351/45 |

OTHER PUBLICATIONS

Cynader, "Competitive Neuronal Interactions Underlying Amblyopia," *Human Neurobiol*, 1:35–39, 1982.

Edelson and Rogers, "Modified MRI may be used to measure amblyopia therapy," *Opthalmology Times*, 42, 2001.

Harwerth, et al., "Effects of Enucleation of the fixating Eye on Strabismic Amblyopia in Monkeys," *Investigative Ophtlahmology & Visual Science*, 27:246–254.

Hoffman and Fine, "Transient no light perception visual acuity after intracameral lidocaine injection," *J Cataract Refract Surg*, 23: 957–958, 1997.

Hoffmann and Lippert, "Recovery of Vision with the Deprived Eye After the Loss of the Non–Deprived Eye in Cats," *Human Neurobiol*, 1:45–48, 1982.

Klaeger–Manzanell, et al., Two step recovery of vision in the amblyopic eye after visual loss and enucleation of the fixing eye, *British Journal of Ophthalmology*, 78:506–507, 1994.

Sabel and Schneider, "The principle of "conversation of total axonal arborizations": massive compensatory sprouting in the hamster subcortical visual system after early tectal lesions," *Exp Brain Res*, 73:505–518, 1988.

Sireteanu, et al., "Human Amblyopia: Consequence of Chronic Interocular Suppression," *Human Neurobiol*, 1:31–33, 1982.

* cited by examiner

*Primary Examiner*—Brian L. Casler
*Assistant Examiner*—Kevin C. Siromns
(74) *Attorney, Agent, or Firm*—Akerman Senterfitt (57) ABSTRACT

A method of improving vision in an amblyopic eye is described in which vision in the dominant eye is reversibly disrupted. The technique promotes improvement of visual acuity in the weaker eye. The disclosed method is particularly suitable for treatment of adult amblyopia. The method also includes several devices suitable for use in the described treatments.

14 Claims, 7 Drawing Sheets

METHOD AND APPARATUS FOR TREATMENT OF AMBLYOPIA

CROSS REFERENCE TO RELATED APPLICATION

The present application claims the priority of U.S. provisional patent application No. 60/340,301, filed Dec. 13, 2001, and entitled "Method and Apparatus for Treatment of Amblyopia."

1.0 BACKGROUND ART

1.1 Field of the Invention

The invention concerns apparatus and methods for treating amblyopic conditions and is particularly directed to methods that correct this visual deficiency in adults.

1.2 Description of Related Art

Amblyopia, Greek for "blunt vision", is the failure of an anatomically intact eye to develop normal visual acuity. Amblyopia affects five to seven million individuals in the United States alone, with an estimated 70,000 new cases annually. Amblyopia accounts for more visual loss in the under-45 age group than all other ocular diseases, including trauma. In the lay press, this condition is often referred to as "lazy eye". The term lazy eye is to be avoided, however, as it may also be used in the lay press to describe strabismus ("crossed" eye) as well. While a crossed eye may become amblyopic (strabismic amblyopia), not all crossed eyes are amblyopic nor are all amblyopic eyes crossed.

Amblyopia represents a failure of the affected eye to develop normal synaptic connections with the visual cortex (Sireteanu, 1982). This is thought to result from an abnormal outcome of the competitive process of visual development. During visual development, the roughly 1.2 million nerve fibers that make up the optic nerve of each eye compete for synaptic connections in the brain (Cynader 1982). Under normal developmental circumstances, the visual input from each eye is roughly equal to that of its counterpart therefore each eye is assigned a proportionately equal number of synapses in the visual processing areas of the brain and allowed to realize its full visual potential. In humans, this process is thought to begin at birth and continues until roughly 8 years of age.

The number of synapses available within a given area of cortex is limited and once this number of synapses is reached, the development of additional synapses cannot occur without the loss or destruction of other synapses in the same cortical area. This phenomenon is known as the conservation of total axonal arborizations (Sabel 1988). In amblyopia, one eye is disadvantaged relative to the contralateral eye. This may be due to the need for spectacle correction in one eye more so than the other (refractive amblyopia), by the presence of a crossed eye (strabismic amblyopia) or by the presence of an obstruction in the visual axis of one eye (cataract, ptosis of the upper eyelid, or presence of an eyelid mass, for example). During visual development, the better-seeing eye is therefore assigned a greater proportion of the available synapses in visual cortex than its poorer seeing counterpart. In this way, the better-seeing eye may control more synapses in the cortex than it needs for optimal vision. With a limited number of synapses available in visual cortex, the poorer-seeing eye is left with fewer synapses than it needs for normal vision. If this situation remains uncorrected beyond the critical period of visual development, these synaptic connections become fixed, and neither correction of the weaker eye's underlying disadvantage nor the patching therapy described below will return the eye to normal visual acuity. If this situation is recognized during the first years of life (before) the critical period of visual development is complete however, treatment is often possible.

The problem is typically addressed in the following manner: First, the underlying condition that initially disadvantaged the weaker eye (i.e., the need for glasses, obstruction by a ptotic eyelid, strabismus, etc) is corrected. Second, the better-seeing eye is temporarily disadvantaged relative to the amblyopic eye. This is usually accomplished via occlusion of the dominant eye with an eye patch or similar occlusive device. In lieu of a patch, it is also possible to use cycloplegic eye drops such as atropine in the dominant eye to cause visual blurring. This practice is sometimes referred to as "pharmacologic patching". In this way, the amblyopic eye is given an opportunity to form sufficient synaptic connections to allow useful vision before the critical period is complete and synaptic connections become fixed.

If occlusion therapy is used too aggressively, however, it is possible to make the previously dominant eye amblyopic. For this reason, regular visual acuity checks are necessary throughout amblyopia therapy. As a general rule, visual acuity is checked in both eyes on a schedule of 1 week per year of patient life. For example, a 1-year old undergoing full-time occlusion therapy would have his or her vision evaluated weekly; a 4-year old undergoing full-time occlusion therapy would have his or her vision evaluated every four weeks. These checkups include an examination to ensure that the underlying cause of the amblyopia (e.g., refractive error, ptotic eyelid, strabismus, etc) is being managed appropriately, as well as an assessment of visual acuity in each eye. In older literate children, this is done with a standard eye chart. In younger children who are verbal but not yet literate, standardized picture charts are used to determine visual acuity. In preverbal children, the task is significantly more difficult and often involves the examiner observing the child's ability to fixate upon and follow a small target with each eye.

Thus the two mainstays of amblyopia management in children are the prevention of any condition that could disadvantage the vision of one eye relative to its counterpart, and occlusive therapy, whether by physical patching or pharmacologic cycloplegia. Occlusive therapy is problematic for several reasons: First, the technique is only effective during the so-called critical period during which the visual system is developing. In humans, this period begins at birth and is largely complete by eight years of age, although this limit is subject to debate. The older the patient is, the less successful occlusive therapy tends to be, with occlusive therapy in adults having little or no significant value.

Second, and of significant importance, keeping an occlusive dressing over the dominant eye of a young child is a challenge for child, parent, and physician alike. Understandably, many children fail occlusive therapy due to noncompliance. This leaves these patients with permanent visual loss in the amblyopic eye, as occlusion therapy is not efficacious in adults and there are currently no effective methods for the treatment of adult amblyopia.

1.3 Deficiencies in the Prior Art

The challenge in an amblyopic patient therefore is to improve vision in the amblyopic eye without causing significant reduction of visual acuity in the dominant eye. There is currently no such therapy available to adult patients or to pediatric patients refractory to occlusion therapy. The lack of a demonstrably effective treatment for adult amblyopia leaves many patients with severely limited, often debilitating, vision. The prevalence of adult amblyopia indicates the need to develop a therapy to improve vision in an amblyopic eye. This is of paramount importance in patients who have sustained vision loss in their dominant non-amblyopic eye from disease or trauma. Significant alleviation of the handicap caused by visual deprivation arising from this condition would allow this population of adults to function more effectively in society and to enjoy a better quality of life.

2.0 SUMMARY OF THE INVENTION

The invention addresses the need for providing a treatment for improving vision in an amblyopic eye. The method utilizes selected drugs to induce a sustained yet reversible interruption of optic nerve transmission in the dominant eye, which is sufficient to allow complete or significant visual recovery in the amblyopic eye. The disclosed procedures are particularly suitable for treatment in adults for whom conventional methods used in children are ineffective.

Accordingly, the invention in one aspect is a method of safely interfering with impulse transmission from the dominant eye to the brain. This is accomplished with a drug that effectively blocks nerve transmission. Many drugs are known to interfere with nerve conduction, including for example, local anesthetics such as lidocaine and bupivicaine; cocaine; bufotoxins; picrotoxin; botulinum toxin; tetrodotoxin; snake venom toxins such as bungarotoxin; dinoflagellate toxins such as those produced by *Pfiesteria pisicida*; electric stimulation; gamma-aminobutyric acid; norepinephrine; levodopa/carbidopa; benzodiazepines; and 4-aminopyridine.

Selection of appropriate drugs may be determined in animal models to assess safety and efficacy. Preferred drugs recognized as effective in blocking nerve transmission are lidocaine and bupivicaine. These agents are considered by one skilled in the art as drugs of choice for reasons of safety and long term history of use. In particular, the safety of these agents in the orbit socket of the human eye is well established. These drugs are routinely used for retrobulbar and peribulbar anesthesia of the eye in a variety of ophthalmic procedures including cataract surgery, glaucoma surgery, and retinovitreal surgery. Preservative-free 1% lidocaine HCL is also routinely used within the eye as an adjunct to topical anesthetics during cataract surgery.

The safety of 1% preservative-free lidocaine in the anterior segment of the eye is well established as the drug is frequently used as an anesthetic adjunct to topical anesthesia in modern cataract surgery. Anecdotal reports of 1% preservative-free lidocaine entering the posterior segment of the eye (Hoffman and Fine, 1997) have demonstrated that the drug blocked transmission of visual signals to the patient's brain as the patient rapidly developed "no light perception" vision. This effect was reversible, however, and vision returned in the eye within hours of discontinuing the drug. The authors report no evidence of retinal toxicity following the exposure to 1% preservative-free lidocaine.

Another aspect of the invention is a method of providing controlled amounts of the selected drug to the targeted nerve. In one embodiment, a device employing a small drug delivery pump directs an appropriate drug through a canula into the orbit (socket) of the dominant eye. A fenestrated canula or catheter, preferably made of flexible, biocompatible material, is placed into the orbit of the dominant eye using one of several maneuvers. The catheter can be inserted without guidance into the orbit over a needle. A similar "blind stick" technique is used to induce peribulbar or retrobulbar anesthesia prior to ocular surgery. The needle is then withdrawn, leaving the catheter in the orbit. The catheter can also be advanced into the orbit under CT (computerized tomography) or fluoroscopic guidance. Finally, guidance of the catheter into the orbit may be facilitated by electronic feedback. The infusion catheter or canula can include a conductive strip allowing the catheter to function as a sensing electrode. Alternatively, the infusion catheter can be introduced over a needle possessing an insulated shaft and a conductive tip such that the needle acts as a sensing electrode. In either case, photic stimulation is provided to the dominant eye thereby producing impulses in its optic nerve which are detected by the electrode as it comes in closer and closer proximity to the optic nerve. In this way, feedback from the electrode allows the surgeon to accurately place the catheter near the optic nerve while feedback from the electrode allows the surgeon to avoid traumatizing the optic nerve with the needle or catheter.

The catheter may also be placed in close proximity to the optic nerve by direct visualization using a surgical approach such as a medial orbitotomy. While more invasive, this method would allow exact placement of the canula near the optic nerve. Using this technique, placement of the canula could be accompanied by optic nerve sheath fenestration, a technique in which a "window" is made into the dural covering of the optic nerve, thereby allowing any infused drugs easier access to the optic nerve.

Following catheter placement, a drug delivery pump supplies an infusion of drug sufficient to decrease or suspend impulse transmission by the optic nerve. The pump is easily miniaturized so that it can be comfortably placed on the neck or behind the ear of the patient or even implanted beneath the conjunctiva with little discomfort or inconvenience. Control of drug delivery can be by manual set in the physician's office, or adjusted automatically through use of a microprocessor. The microprocessor can be adapted to detect signals from the dominant eye to the optic nerve so that an amount of drug can be administered that is effective to prevent or inhibit the transmission of impulses from the dominant eye to the brain via the optic nerve.

In another embodiment, an appropriately sized canula (similar to the trans-pars plana infusion canula currently used in retinal-vitreous surgery or the trans-pars plana shunt tube used in glaucoma surgery for example) is fixated to the eye using standard surgical techniques. This canula is then connected to a small drug delivery pump, which can be sutured to the sclera and implanted beneath the conjunctiva in the same fashion as the plate of a glaucoma shunt device. The pump then delivers a nerve-blocking agent intraocularly via the canula, thereby interrupting transmission of nerve impulses from the dominant eye to the brain. The pump can deliver a nerve-blocking drug at a fixed, preset rate or may be controlled by any of a number of means including but not limited to radio frequency, optical sensor, inductive control, or manual manipulation across the conjunctiva. The drug delivery pump and canula remain safely implanted beneath the conjunctiva until treatment is complete, after which time the pump and canula can be removed.

In another embodiment, a nerve-blocking agent is delivered intraocularly via an intraocular drug delivery system. This may be accomplished by a variety of methods including but not limited to: time-release inserts, osmotic pumps, conventional electromechanical pumps, or pumps which make use of Micro Electro Mechanical Systems (MEMS) microtechnology.

In yet another embodiment a drug delivery device is implanted within the orbit to administer an appropriate drug to the optic nerve of the dominant eye. A variety of drug delivery devices could be implanted within the orbit including but not limited to: time-release preparations of the drug of choice (pellets of drug combined with a biodegradable matrix, for example), osmotic drug delivery pumps, miniaturized conventional drug delivery pump and pumps which make use of Micro Electro Mechanical Systems (MEMS) technology.

Finally, when electricity is the drug chosen to modulate optic nerve function, a biocompatible electrode, preferably flexible in construction, is placed in the orbit in proximity to the optic nerve instead of a drug delivery catheter. Placement of the electrode may be guided by the methods described above for catheter placement. In lieu of a drug delivery pump, an electrical stimulator circuit is connected to the electrode and used to deliver a current sufficient to interrupt optic nerve transmission.

The disclosed method is a method of treating amblyopia by administering a denervating drug to a dominant eye, monitoring visual acuity in the amblyopic eye, and reversing denervation upon achieving a selected degree of visual acuity in a corresponding amblyopic eye.

3.0 BRIEF DESCRIPTION OF THE DRAWINGS

The drawings form part of the present specification and are included to further demonstrate certain aspects of the present invention. The invention may be better understood by reference to one or more of the following drawings in combination with the detailed description of specific embodiments presented herein.

4.0 DETAILED DESCRIPTION OF ILLUSTRATIVE EMBODIMENTS

The invention provides a method of treatment for recovery from amblyopia. Initially, optic nerve function in the dominant/non-amblyopic eye is interrupted in a controlled manner to cause the amblyopic eye to improve. Once the appropriate degree of improvement is observed, optic nerve function is restored with the result of significantly improved visual functioning in the amblyopic eye without significantly diminishing vision in the dominant eye.

The need for such a treatment is of particular importance to patients who have suffered a significant visual loss in their previously dominant eye. Reduced visual acuity in the dominant eye may be the result of a variety of conditions including but not limited to: corneal opacification, retinal disease, and optic nerve disease. Diseases known to cause corneal opacification include herpes simplex keratitis, varicella zoster keratitis, bacterial keratitis, fungal keratitis, protozoal keratitis, chemical burns, corneal dystrophies, bullous keratopathy, trauma, rejected corneal transplant, and autoimmune keratitis. Retinal diseases that cause visual loss include macular hole, macular edema, macular pucker, retinal detachment, Age-Related Macular Degeneration (ARMD), diabetic retinopathy, choroidal neovascular membranes, retinal vein occlusion, retinal artery occlusion, retinitis, choroiditis, endophthalmitis, and ocular tumor. Optic nerve diseases that cause visual loss include, ischemic optic neuropathy, optic neuritis, glaucoma, and traumatic optic neuropathy.

As discussed earlier, once the "critical period" of visual development is complete, synapses in visual cortex become fixed. In humans, this process is generally considered to be complete by eight years of age. After this time, occlusion therapy is essentially ineffective in restoring visual acuity in an amblyopic eye. The current understanding of this phenomenon is as follows: During the critical period of visual development, the visual system is still relatively undeveloped and synapses are still forming between the afferent visual pathways and higher visual centers such as visual cortex.

The principle of the conservation of total axonal arborizations states that within a given area of cortex, a limited number of synaptic connections are available. If both eyes provide images of equal quality to the brain, each eye will come to control an equal proportion of the available synapses in the brain and normal visual acuity will be present in each eye. If one eye is disadvantaged relative to the other, the eye which produces the clearer image will come to control a significantly greater proportion of the available synapses in the brain while the eye producing the image of lesser quality will come to control a lesser proportion of available synapses. In this way, the eye controlling the greater proportion of synapses will develop normal visual acuity while the eye controlling the lesser proportion will develop subnormal acuity (amblyopia).

Once the critical period is complete, neural tone (background activity of a neuron which is present even when the neuron is not actively firing) maintains existing synapses even when their constituent neurons are not actively firing impulses. This is analogous to the neural tone, which keeps synaptic connections between motor nerves and skeletal muscle intact even when the muscle is not actively contracting. This phenomenon of neural tone explains why occlusion therapy does not work in adults. Once the critical period of visual development is complete, neuronal tone maintains synapses between the dominant eye and visual cortex even when the dominant eye is occluded or otherwise fails to provide a clear image to the brain.

The inventor reasoned that if new synapses are to be formed between an amblyopic eye and visual cortex, temporary interruption of neural tone between the dominant eye and the visual cortex must be achieved. Interruption of this neuronal tone allows dissolution of some of the synapses between the dominant eye and the visual cortex, and makes these synaptic connections available for the amblyopic eye. This, in essence, temporarily restores some of the synaptic plasticity, which is present during the critical period of visual development. A review of the literature supporting this process is now provided:

Studies in amblyopic animals (Harwerth et al 1986, Hoffmann and Lippert 1982) have demonstrated that enucleation (surgical removal) of the dominant eye is sufficient to allow recovery of vision in the amblyopic eye even when simple occlusion of the dominant eye had failed to bring about any such improvement. The theory underlying this phenomenon is that by disrupting the optic nerve of the dominant eye, the neural tone, which maintains synapses between the dominant eye and visual cortex is released. Synapses between the previously dominant eye and visual cortex break down, making synapses available for the amblyopic eye.

The applicability of this phenomenon to human subjects is supported by the "2-step" recovery of vision in a human subject described by Klaeger-Manzanell et al (1994). Since childhood, this patient had a densely amblyopic right eye with a best-corrected visual acuity of 20/200. At 44 years of age, he sustained a penetrating injury to his dominant left eye that reduced the best-corrected visual acuity in this eye to "count fingers at 6 feet". Over a period of 6 weeks after his injury to the left eye, the vision in his amblyopic right eye improved slightly to 20/80 and remained fixed at this level for a period of 13 months. Subsequently the injured left eye became painful and required enucleation (surgical removal of the eye) in order to control the patient's pain. Although the vision in the amblyopic right eye had remained stable for 13 months prior to enucleation of the previously dominant left eye, it improved to 20/40 within three weeks of the enucleation and further improved to 20/30 within 4 months.

Further evidence that denervation of the dominant eye permits visual recovery in an amblyopic eye is an as yet unpublished account of a similar "2-step" recovery from amblyopia in an adult human subject. At 6 years of age, the patient sustained trauma to his right eye, which resulted in amblyopia and a visual acuity of "count fingers at one foot". Vision in the patient's dominant left eye was 20/20 until the age of 78, when the patient developed a viral keratitis of the cornea of his left eye. This infection was further complicated by a fungal superinfection, which left the patient with a dense corneal scar and vision in the "count fingers" range. Despite deprivation of useful vision in the formerly dominant left eye for a period of 4 months, the best-corrected vision in the amblyopic eye was still only 20/400. This patient then experienced a disruption of optic nerve function in his previously dominant left eye. Unlike the patient described by Klaeger-Manzanell et al (1994), whose optic nerve was transected surgically during enucleation, this patient's optic nerve was disrupted by markedly elevated intraocular pressure resulting in absolute glaucoma and death of the left optic nerve. Following this event, vision in the patient's amblyopic eye improved from 20/400 to 20/60 over a period of 2 months and further improved to 20/25 by 5 months. In both animal models and in the natural human experiments described above, occlusion or visual deprivation of the dominant eye was not sufficient to allow for visual recovery in the amblyopic eye of adults. Only after disruption of signal transmission from the eye to the brain via the optic nerve was the amblyopic eye able to significantly recover.

Animal studies have demonstrated that new cortical synapses "sprout" in response to denervation (Sabel and Schneider, 1988). This denervation-induced synaptic plasticity appears to have been responsible for the recovery of vision in the amblyopic eye of patient described by Klaeger-Manzanell et al., as well as in the amblyopic eye of a patient observed by the inventor. Based on these observations, the inventor reasons that controlled and reversible denervation of the dominant eye will allow sufficient axonal sprouting for visual recovery in the amblyopic eye.

4.1 DETAILED DESCRIPTION OF THE PREFERRED EMBODIMENTS

Figure 1:
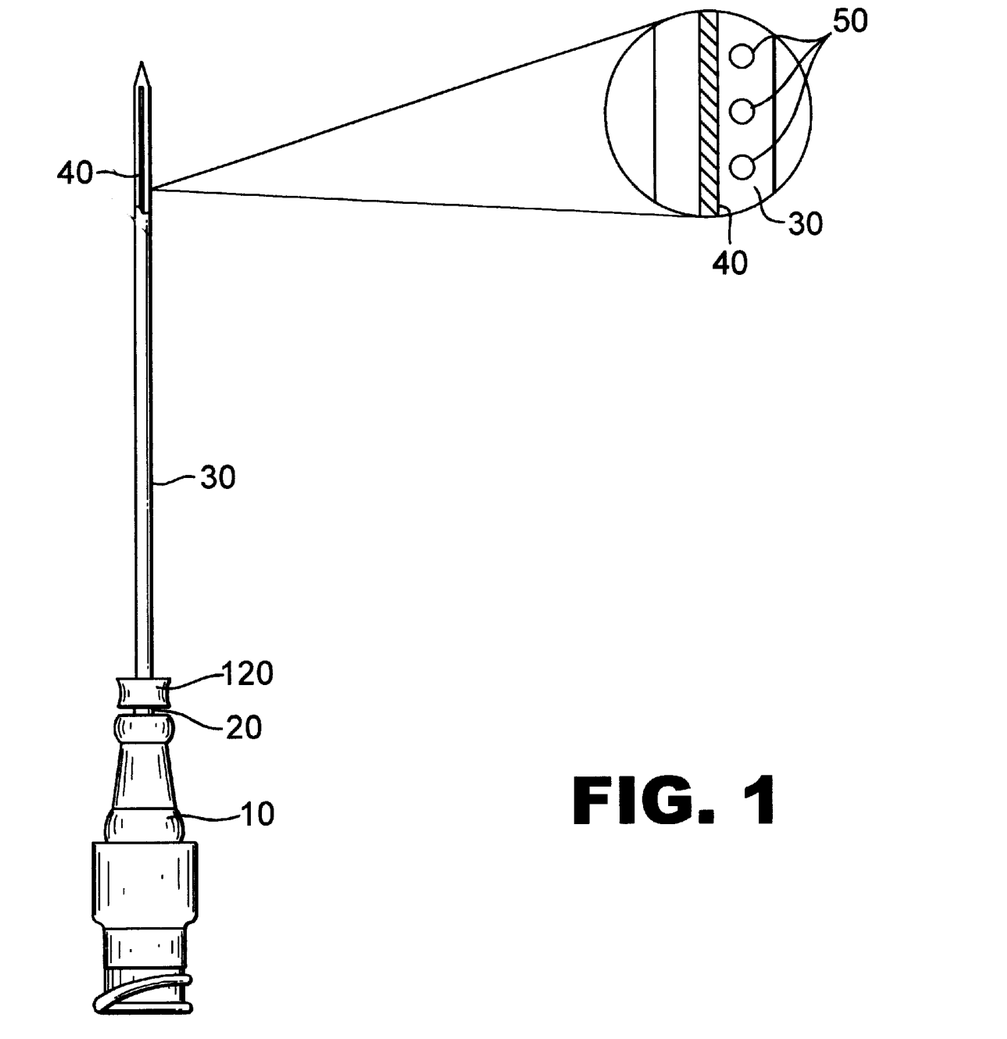
FIG. 1 is a side view of one embodiment of a drug delivery needle and catheter.

Referring now to the drawings wherein the illustrations are for purposes of demonstrating preferred embodiments of the invention and not for purposes of limiting the same: FIG. 1 illustrates a flexible biocompatible catheter (30) over the shaft of a needle (20) with hub (10). This catheter possesses a conductive strip (40) on its surface. This conductive strip may serve a dual purpose. During placement of the catheter into the orbit, the strip is connected to monitoring equipment that detects the firing of the optic nerve as the eye is stimulated by a strobe light or other appropriate stimulus. The detected signal grows stronger as the catheter is placed closer to the optic nerve of the eye. This allows the surgeon to place the catheter very close to the optic nerve without damaging the optic nerve with the catheter or needle. After catheter placement is complete and the needle is withdrawn, the same conductive strip can function as a feedback electrode, allowing the surgeon to monitor whether the administered drug is adequately blocking the optic nerve. A plurality of appropriately placed fenestrations (50) in the canula direct the administered drug towards the optic nerve. In this way, drug delivery to the target nerve is maximized while potential toxicity of the drug elsewhere in the orbit is minimized. A connector (120) allows for connection of the catheter to a drug delivery device, either directly or via extension tubing.

Figure 2A:
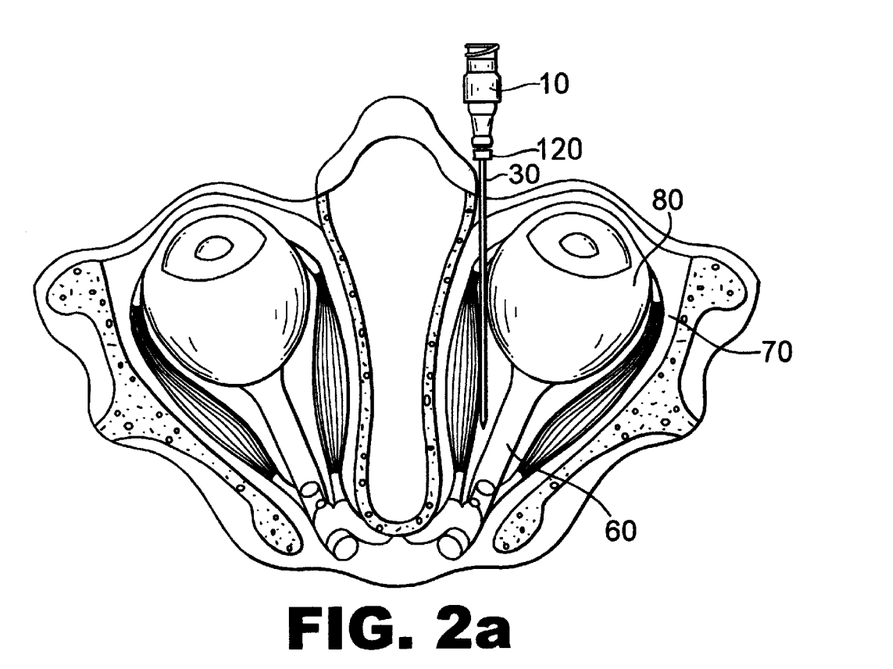
FIG. 2 is an axial view of a human head showing the drug delivery canula in place in the orbit.
Figure 2B:
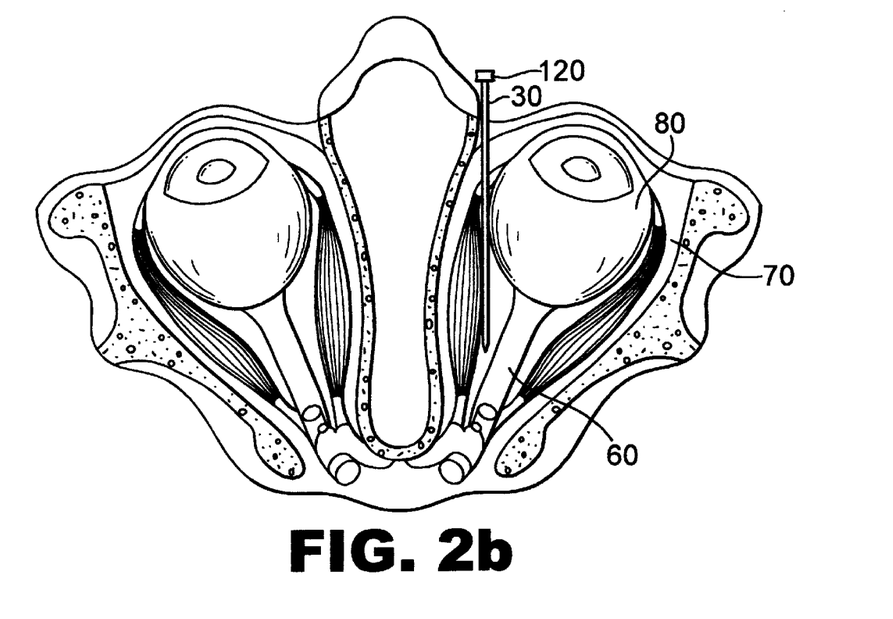

FIGS. 2a and 2b illustrate an axial view through the head of a human subject at the level of the mid-orbit. FIG. 2a shows the drug delivery catheter (30) being advanced into the orbit (70) over a needle. FIG. 2b shows the catheter (30) in place along the optic nerve (60) of the eye (80) after the needle has been withdrawn.

Figure 3:
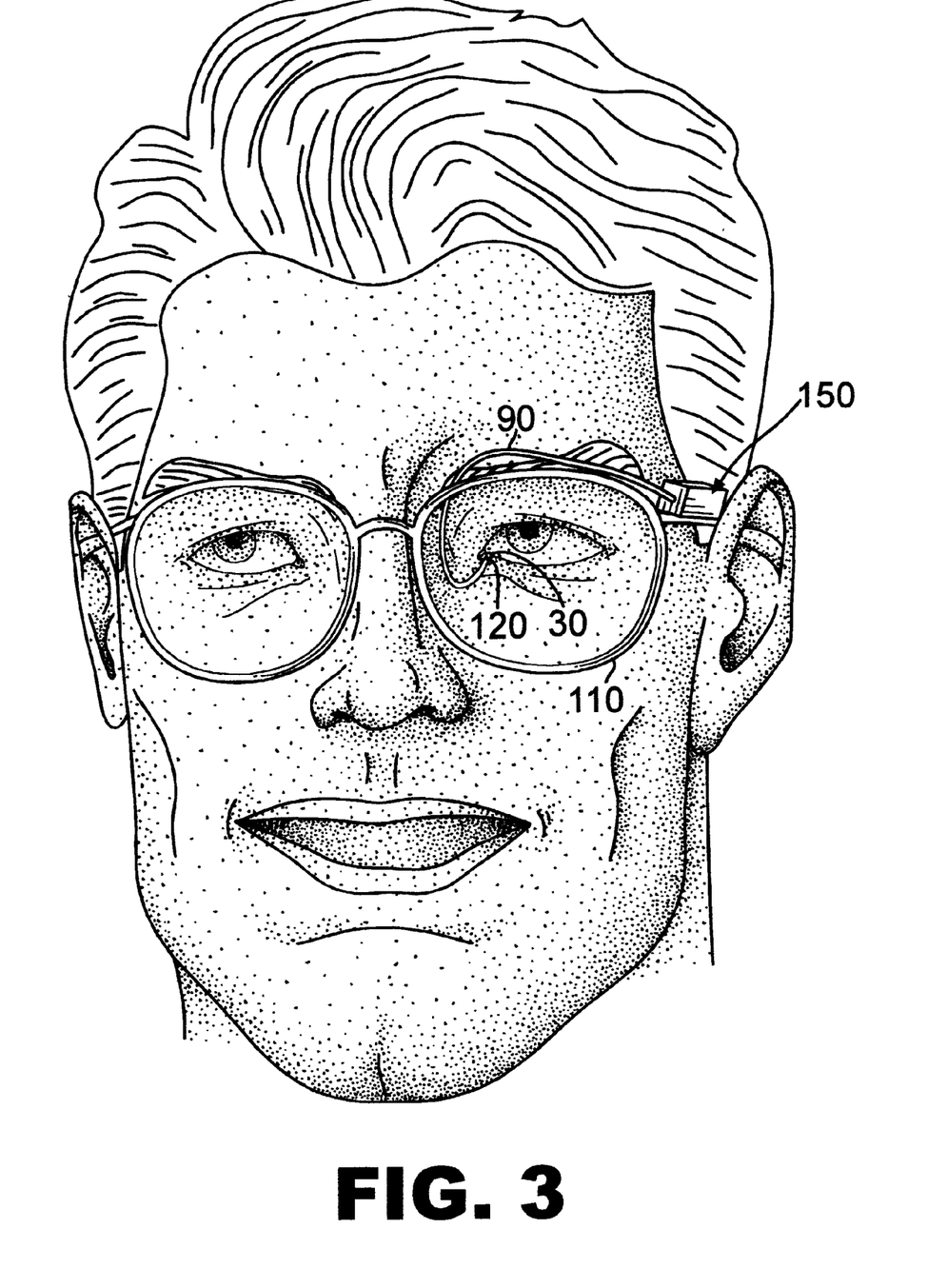
FIG. 3 is a frontal view of a human patient showing a drug-delivery system mounted on the patient's spectacle frame. The drug delivery canula is visible as it exits the patient's orbit.

FIG. 3 illustrates a frontal view of a patient with the drug delivery catheter (30) in place. The catheter's distal tip has been placed adjacent to the patient's optic nerve while the proximal end of the catheter is visible as it exits the patient's orbit. An appropriate length of tubing (90) joins the catheter's connector (120) to a drug delivery device (150). In this embodiment, the drug delivery device and associated tubing are mounted to the patient's spectacle frame (110) for patient convenience and comfort. Alternatively, the drug delivery device (150) may be fashioned so as to be worn comfortably behind the patient's ear in much the same manner as a behind-the-ear style hearing aid.

Figure 4:
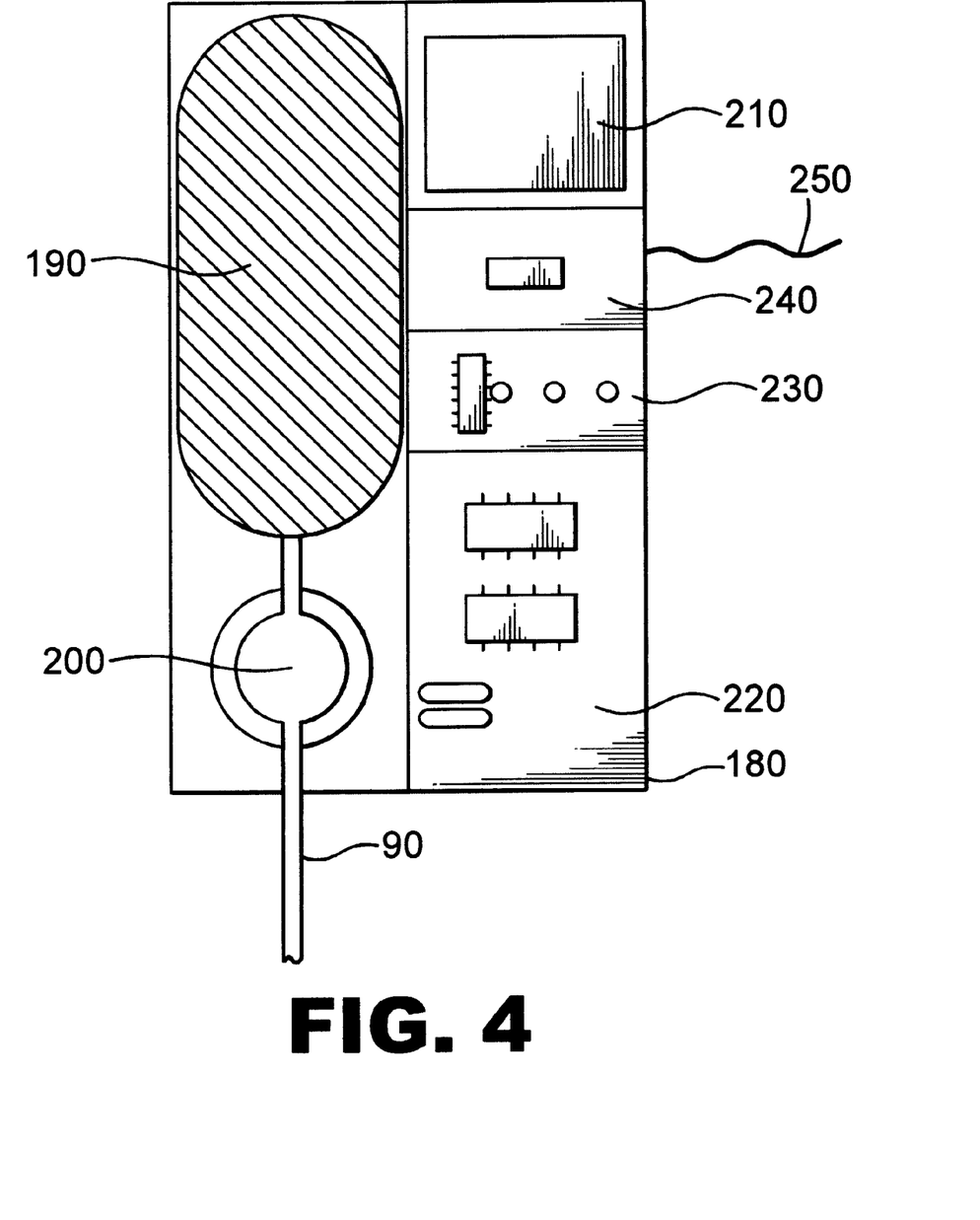
FIG. 4 is a schematized view of a preferred drug delivery system.

FIG. 4 illustrates a schematized view of a preferred embodiment of a drug delivery device. In this embodiment, the system comprises a drug reservoir (190), which contains the drug to be administered. A pump (200) conveys the drug from the reservoir (190) to an appropriate delivery canula, ideally via a length of flexible tubing (90). The operation of the pump is controlled by pump-control circuitry (220). The settings of this pump control circuitry are adjusted via the pump control interface (230). The nature of this interface is selected according to the particular embodiment of the invention in which it is to be used. In embodiments in which the drug delivery device is to be used externally (in the spectacle-mounted arrangement shown in FIG. 3, for example) this interface can comprise one or more buttons, switches, rheostats, or other manual mechanical controls. In embodiments in which the drug delivery device is to be implanted within the body (beneath the conjunctiva as in FIG. 5 or within the eye itself as in FIG. 6, for example) this interface may take the form of a radio frequency receiver, inductive receiver, or optical receiver. When the drug delivery device is to be implanted beneath the conjunctiva, mechanical controls of a size and shape conducive to being manipulated across the conjunctival surface and protected by a biocompatible material may be utilized in the pump control interface (230). Mechanical switches sensitive to the mechanodisruptive force of an Nd:YAG laser can be used in the pump control interface in embodiments in which the drug delivery system is to be implanted intraocularly.

In embodiments in which control of the drug delivery device is in some part modulated by feedback from the optic nerve, optic nerve feedback control circuitry (240) receives electrical impulses from an optic nerve sensing electrode (250), which lies in close proximity to the optic nerve. In an embodiment of the invention, which makes use of a drug delivery canula in the orbit (FIGS. 1, 2a, 2b, 3 for example), this sensing electrode (250) is continuous with the sensing electrode (40) integrated into the drug delivery catheter (30). While this function of the drug delivery system may be used in clinical practice, it is expected to prove more useful during the testing of new drugs as such drugs become available.

A battery or other suitable power source (210) provides power to the components of the drug delivery device. In embodiments in which the drug delivery device is to be implanted within the tissues of the body, the device is encased within a suitable biocompatible case (180).

Figure 5:
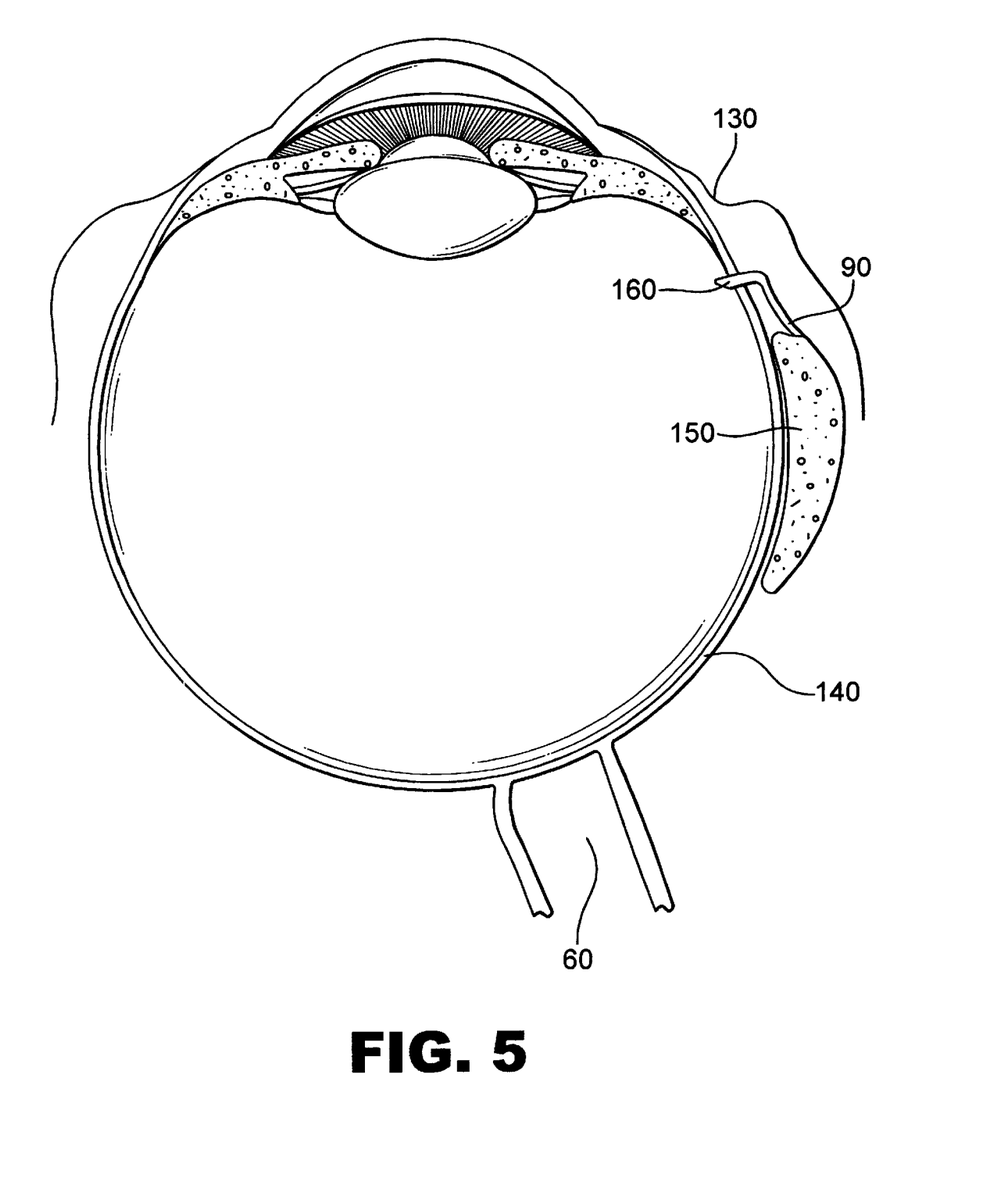
FIG. 5 is a partial cross-sectional view of an eye showing a second embodiment of the present invention in which the drug delivery system and canula are implanted beneath the conjunctiva of the eye.

FIG. 5 is a partial cross-sectional view of a human eye demonstrating an embodiment of the present method and apparatus in which a drug delivery system is implanted beneath the conjunctiva of the eye. In this embodiment, the drug delivery system (150) is fashioned to follow the contour of the eye for patient comfort and is implanted beneath the conjunctiva of the eye (130) using established surgical techniques already in use for the placement of glaucoma shunts. A drug delivery system (150), possessing some or all of the components described in FIG. 4, is connected via an appropriate length of biocompatible tubing (90) to an infusion canula (160). In this embodiment, the canula tip passes through a small incision in the sclera of the eye (140), (preferably in the pars plana region) and is held in place with sutures. The surgical techniques for placement of such a canula are well established as they are currently utilized both in the implantation of trans-pars plana glaucoma shunts and in the placement of trans-pars plana infusion canulas during standard trans-pars plana vitrectomy surgery. Placement of the canula may be accompanied by vitrectomy as needed to prevent occlusion of the canula by vitreous and/or to facilitate drug delivery to the optic nerve (60).

Figure 6:
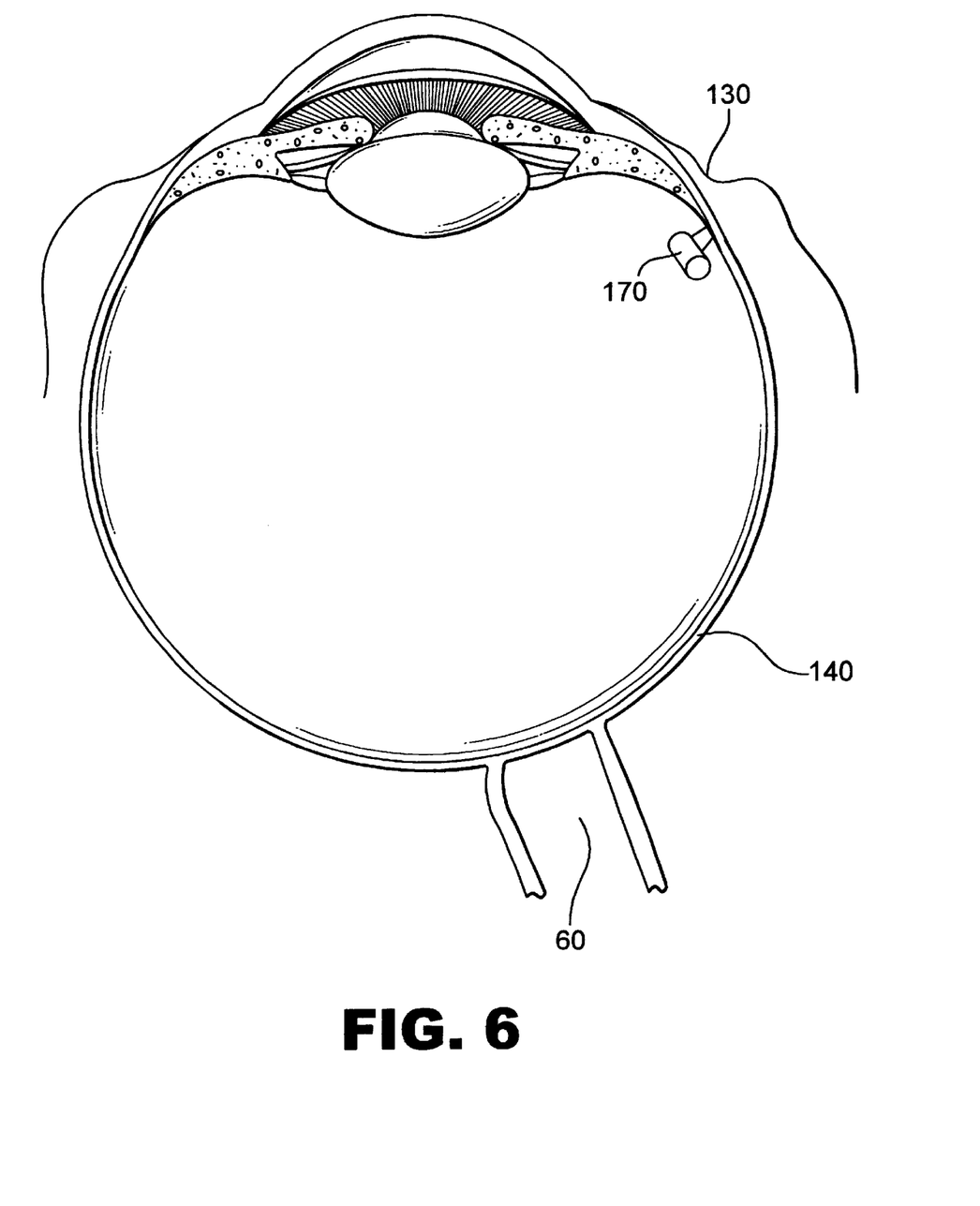
FIG. 6 is a partial cross-sectional view of an eye showing a third embodiment of the present invention in which the drug delivery is accomplished by an intraocular drug delivery system.

FIG. 6 is a partial cross-sectional view of a human eye demonstrating an embodiment of the present method and apparatus for the treatment of amblyopia. In this embodiment a time-release drug delivery device (170) is implanted within the eyeball itself. Time-release drug delivery devices are already in use for delivery of various medications to the posterior segment of the eye. One such device, Vitrasert® is manufactured by Bausch and Lomb (One Bausch and Lomb Place, Rochester, N.Y., 14604-2701, U.S.A.). Vitrasert® uses the antiviral drug ganciclovir in a time-release insert and is FDA approved for the treatment of cytomegalovirus retinitis. Similarly, the Envision TD™ manufactured by Bausch and Lomb (One Bausch and Lomb Place, Rochester, N.Y., 14604-2701, U.S.A.) and Control Delivery Systems Inc. (313 Pleasant Street, Watertown, Mass., 02472, U.S.A.) comprises an intraocular time-release drug delivery insert, which liberates the steroid fluocinolone acetonide into the posterior segment of the eye. This device is currently in FDA trials for the treatment of posterior uveitis, diabetic macular edema, and age-related macular degeneration. These and similar systems may be readily adapted to the delivery of nerve blocking agents such as lidocaine to the optic nerve and/or retina of the eye.

Figure 7:
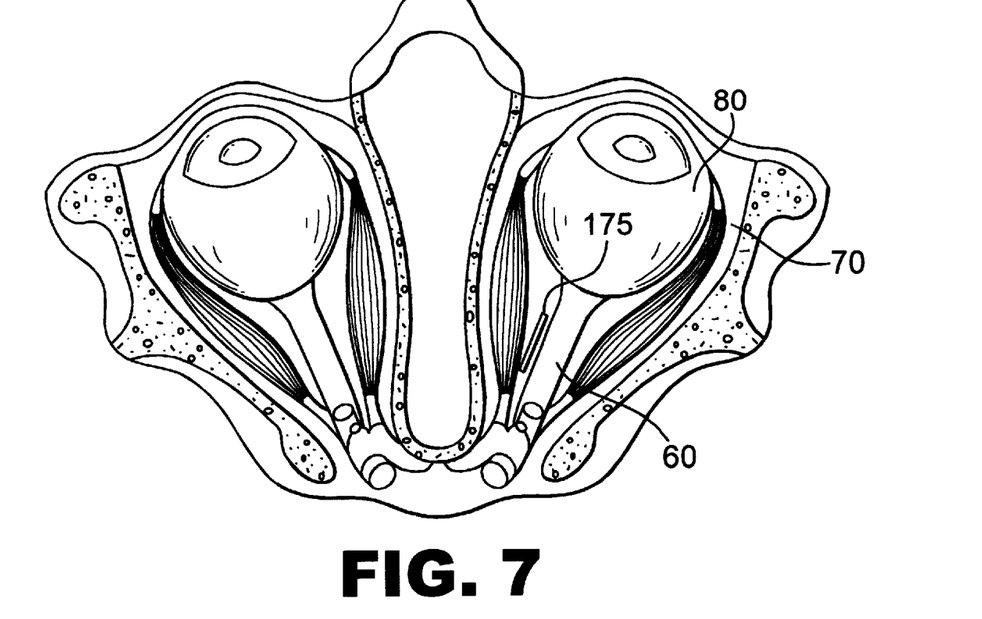
FIG. 7 is an axial view of a human head showing a fourth embodiment of the present invention in which a drug delivery system is implanted within the patient's orbit.

FIG. 7 is an axial view through the head of a human subject at the level of the mid-orbit illustrating an embodiment of the present method and apparatus for the treatment of amblyopia. In this embodiment, a drug delivery device (175) is implanted within the orbit near the optic nerve (60). Implantation may be via surgical orbitotomy or may be accomplished using a needle, trocar, or similar implement to implant the drug delivery system to its target in the orbit. To facilitate placement near the optic nerve and minimize the risk of trauma to the nerve, placement may be directed by CT or fluoroscopic guidance or may be accomplished using an instrument possessing a feedback electrode as described in section 2.0 for the placement of drug delivery catheters. Once in place, the drug delivery device releases a nerve-blocking agent such as lidocaine to the optic nerve of the dominant eye. In this way, a sustained but reversible block of signal transmission from the dominant eye to the brain is achieved. Several existing drug delivery systems could be readily modified to serve this end. Nerve blocking agents such as lidocaine can be compounded as depot or delayed-release agents through a variety of methods including microsphere preparations (for example, Microdur™ manufactured by Durect Corporation, 10261 Bubb Road, Building A, Cupertino, Calif., 95014-4166, U.S.A.), or binding with a biodegradable matrix. A miniaturized drug delivery pump such as the one illustrated in FIG. 4 could also be implanted directly into the orbit. Miniaturization can be accomplished using standard electronic components or Micro Electro Mechanical Systems (MEMS) technology. Osmotic pumps can also be manufactured of an appropriate size and shape for implantation in the orbit. Such osmotic drug delivery pumps are manufactured by the Durect Corporation Cupertino, Calif., 95014-4166, U.S.A.) under the trade name Duros®.

Figure 8:
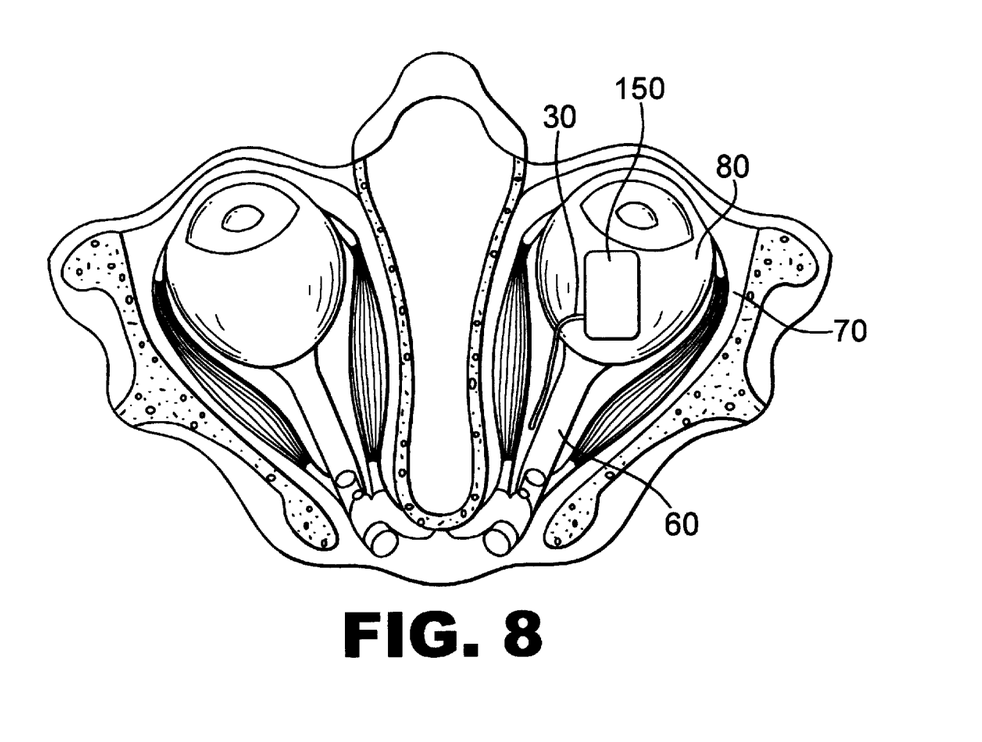
FIG. 8 is an axial view of a human head showing a drug delivery canula in place in the orbit. A drug delivery system is shown sutured to the eyeball within the orbit.

FIG. 8 is an axial view through the head of a human subject at the level of the mid-orbit demonstrating an embodiment of the present invention. In this embodiment, a drug delivery canula (30) is placed in the posterior orbit (socket) adjacent the optic nerve (60). A drug delivery system (150) is sutured to the eyeball (80) and is enclosed beneath the conjunctiva (not visible in this view). The drug delivery system (150) conveys a nerve-blocking agent such as lidocaine to the optic nerve (60) via the drug delivery canula (30).]

5.0 EXAMPLES

The following examples are included to demonstrate preferred embodiments of the invention. It should be appreciated by those of skill in the art that the techniques disclosed in the examples which follow represent techniques discovered by the Inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Safety and efficacy of the disclosed therapy will be verified in the laboratory prior to being used as a therapy in humans. Several reliable animal models of amblyopia have been described in non-human primates, sheep, goats, canines and felines among others. These models induce amblyopia by depriving one eye of vision during the critical period of the animal's visual development. This can be accomplished by surgically closing the lids of one eye (occlusion/deprivation amblyopia), performing eye muscle surgery to cause markedly crossed eyes (strabismic amblyopia), or placing a strong contact lens or spectacle lens in front of one eye to induce refractive error (refractive amblyopia). These models can readily be adapted to refining the disclosed method as well as the described variations in the devices employed for administration of a denervating drug.

The technique of optokinetic nystagmus (OKN) can be used to safely and humanely test the efficacy of the disclosed device and drugs in animal models without the need for costly and time-consuming behavioral training and testing. In this well established technique, a pattern of alternating black and white bands or squares are displayed to the subject using a rotating drum or a video display screen. If the test subject is able to see the stimuli, the eye being tested will involuntarily "chase" the squares, causing the rhythmic eye movements of nystagmus, which are easily visible to an examiner. The size of the presented stimuli is then sequentially reduced until nystagmus is no longer observed. The visual acuity of the test subject can then be estimated using standardized tables to convert the smallest stimulus size, which produced nystagmus into visual acuity.

Another method of objectively quantifying vision in non-verbal or animal subjects is with Visually Evoked Potentials or VEP's. Also a well established technique, this method uses a pattern of alternating squares on a video screen as a stimulus (similar to OKN) and uses the presence or absence of visual cortex activity as the objective indication of whether the stimulus was perceived or not. This brain activity is monitored using a series of electrodes placed on the scalp, much like a simplified version of the electroencephalogram. By noting the smallest stimulus size that causes an encephalographic response from the subject's visual cortex and comparing this to standardized tables, the subject's visual acuity can be determined.

Finally, vision in test subjects may be assessed using functional Magnetic Resonance Imaging (fMRI). This technique can non-invasively measure the metabolic activity of the visual cortex of the brain, a variable shown to be reduced in human amblyopic patients (Edelson and Rogers 2001). Progress of amblyopia treatment in animal models or in human subjects may be determined by periodically following changes in the metabolic activity of the visual cortex throughout the treatment.

The period of time for treatment is expected to vary depending on the age and physical condition of the patient as well as the length of time for the amblyopic eye to develop synaptic connections with visual cortex. Given the time course of the two natural experiments in humans described earlier, it is expected that treatment will likely require weeks to months in order to obtain maximal visual improvement in the amblyopic eye.

Following refinement of this system in animals, limited clinical trials in humans would be most safely conducted in amblyopic patients who have sustained injury or disease to their dominant eye, and presently suffer severe visual impairment. Visually, this population of patients has very little to lose and much to gain from the disclosed system. Several cases of "ideal" trial patients are presented below:

5.1 Example 1

Trauma to Dominant Eye

A 33 year-old male has a history of dense (20/200) amblyopia in the right eye. He was 20/20 in his dominant left eye prior to a motor vehicle accident in which he sustained blunt trauma with extensive choroidal hemorrhage to his left eye. One year following his injury, he has 20/200 vision in his amblyopic right eye and 20/400 in his previously dominant left eye. The patient wishes to improve vision in his amblyopic right eye to permit reading, allow him to return to work, and possibly allow him to drive. A drug delivery canula is placed through the pars plana of the formerly dominant left eye using a standard trans-pars plana vitrectomy technique. This canula is connected to a small drug delivery pump, which is then implanted beneath the conjunctiva of left eye. A nerve-blocking agent in this case 1% preservative-free lidocaine, is delivered to the eye in sufficient quantity to block transmission of impulses from the dominant left eye to the brain. The patient is examined on post-operative day one to ensure that he tolerated the procedure and shows no evidence of infection. Drug delivery to the left eye continues and the patient is re-evaluated on a weekly basis. Treatment is continued as long as vision in the amblyopic eye continues to improve. As visual acuity in the amblyopic eye plateaus, drug delivery to the dominant eye is discontinued. The pump and canula can then be removed.

5.2 Example 2

Corneal Scarring in Dominant Eye

A 43 year-old female with a history of amblyopia in her right eye (20/100) develops HSV (Herpes Simplex Virus) keratitis in her dominant (20/20) left eye. Dense corneal scars result in 20/200 vision in her dominant left eye. Multiple corneal transplants are attempted in the patient's dominant eye and fail due to recurrent HSV. The patient is left with 20/100 vision in her amblyopic eye and "count fingers" vision in her right eye. Likewise, this patient wishes to improve the vision in her amblyopic eye, preferably to levels compatible with safely driving an automobile. In the operating room, a flexible catheter is positioned in the orbit (socket) of the patient's dominant left eye adjacent to the optic nerve. This catheter is then connected via a segment of tubing to a drug delivery pump that is then sutured to the sclera and implanted beneath the conjunctiva of the eye. The pump delivers a reversible denervating drug, in this case 0.50% bupivicaine, to the optic nerve of the dominant eye, allowing recovery of vision in the amblyopic eye. Therapy is discontinued as visual acuity in the amblyopic eye plateaus.

5.3 Example 3

Penetrating Trauma to a Dominant Eye

A 13 year-old male with a history of amblyopia in his left eye (20/200 visual acuity) was using a lawn mower when it ejected a stone, which struck and penetrated his dominant right eye (20/15 visual acuity). Following surgical repair, he is left with "light perception only" vision in his dominant right eye. The patient desires to improve the vision in his amblyopic eye so as to resume normal activities of daily living, including attending school. As with most patients who sustain severe ocular trauma, this patient requires multiple surgical interventions to save the eye and what little visual acuity remains. During a retinal detachment repair of the traumatized dominant right eye, an intraocular drug delivery insert is implanted in the eye using standard surgical techniques. The insert delivers a reversible denervating agent such as 1% preservative-free lidocaine to the dominant eye, allowing recovery of vision in the amblyopic eye. Therapy is discontinued when visual acuity in the amblyopic eye plateaus.

5.4 Example 4

Loss of Vision in a Dominant Eye Secondary to Cancer or the Side Effects of Cancer Therapy Cancer is potential cause of loss of vision in a patient's dominant eye. This can be a direct result of the tumor itself as in the case of primary choroidal melanoma, a potentially fatal primary tumor of the eye, which is almost always unilateral. Vision loss can also be secondary to cancer treatment as is the case with radiation retinopathy seen after external beam radiation for extensive skin cancers of the face and orbit. The methods and treatment disclosed are expected to be applicable in these cases to improve vision in the non-dominant eye.

5.5 Example 5

Loss of Dominant Eye from CMV Retinitis

Immunosuppressed patients particularly those suffering from Human Immunodeficiency Virus/Acquired Immunodeficiency Syndrome (HIV/AIDS), become susceptible to an opportunistic viral infection of the retina known as cytomegalovirus (CMV) retinitis. HIV/AIDS patients are also at risk for vision loss from a retinal disease known as "HIV retinopathy". In situations where such conditions have damaged the vision in an amblyopic patient's dominant eye, the disclosed device may be used to advance the rehabilitation of useful vision in the patient's amblyopic eye.

The above description contains specificities, which should not be construed as limitations on the scope of the invention, but rather as an exemplification of one preferred embodiment thereof, with other variations possible. Such variations might include, but are not limited to, the use of drugs other than those previously mentioned (including the use of electricity as a drug), the use of a neurostimulator drug in the orbit of the amblyopic eye as opposed to an inhibitory drug in the dominant eye, and the combination of both systems.

6.0 REFERENCES

The following literature citations as well as those cited in the text are incorporated in pertinent part by reference herein for the reasons cited in the text.

Cynader, M. S. competitive Neuronal Interactions underlying amblyopia. Human Neurobiol. 1982; 1:35–39.

Harwerth, Ronald S., Smith III Earl L, Duncan Gary C, Crawford, M L J and von Noorden Gunter K. Effects of enucleation of the fixating eye on strabismic amblyopia in monkeys. Investigative Ophthalmology and visual science 1986; 27:246–254.

Hoffmann, K. P. and Lippert, P. Recovery of vision with the deprived eye after the loss of the nondeprived eye in cats. Human Neurobiol. 1982;1:45–48.

Hoffman, R. S. and Fine, I. H. Transient no light perception visual acuity after intracameral lidocaine injection. J Cataract Refract Surg 1997, July–August;23(6):957–8).

Klaeger-Manzanell Corina, Hoyt Creig S. and Good William V. Two step recovery of vision in the amblyopic eye after visual loss and enucleation of the fixing eye. Br. J. Ophthalmol. 1994: 78:506–507.

Sabel, B. S. and Schneider, G. E. The principle of "conservation of total axonal arborizations: massive compensatory sprouting in the hamster subcortical visual system after early tectal lesions". Exp. Brain Res. 1988; 73:505–518.

Sireteanu, R., Human amblyopia: Consequence of Chronic Interocular Suppression. *Human Neurobiol.* 1982; 1:31–33.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions, in the or in the sequence of steps of the method described herein and in the modification of the apparatus connected with the methods and compositions without departing from the concept, spirit and scope of the invention. More specifically, it will be apparent that certain agents which are both chemically and physiologically related may be added to, combined with or substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A method for improving vision in an amblyopic eye, comprising denervating the dominant eye of a subject for a period of time sufficient to allow improvement of visual acuity in the amblyopic eye.

2. The method of claim 1 wherein the denervating is with an agent selected from the group consisting of lidocaine, bupivicaine, cocaine, bufotoxin, picrotoxin, botulinum toxin, tetrodotoxin, conotoxin, bungarotoxin, dinoflagellate toxin, electricity, gamma-aminobutyric acid, norepinephrine, benzodiazepine, 4-aminopryidine, I levodopa and carbidopa.

3. The method of claim 2 wherein the denervating agent is a local anaesthetic.

4. The method of claim 3 wherein the local anaesthetic is licocaine or bupivicaine.

5. The method of claim 1 wherein the denervating agent is administered periodically.

6. The method of claim 1 wherein the denervating agent is administered continuously.

7. The method of claim 1 further comprising testing for visual acuity in the amblyopic eye at selected times after denervating the dominant eye.

8. The method of claim 1 wherein the subject has diminished acuity in the dominant eye.

9. The method of claim 8 wherein diminished acuity is the result of trauma, retinal disease, corneal disease, HIV/AIDS or a HIV/AIDS related disease, choroid disease or optic nerve disease.

10. The method of claim 8 wherein the diminished acuity is caused by cancer.

11. The method of claim 1 wherein the delivering of a denervating drug to the subject's dominant eye is with an intraocular insert.

12. The method of claim 1 wherein the denervating agent reversibly inhibits or reduces signal to the optic nerve.

13. The method of claim 1 wherein delivery is into the orbit or intraocularly.

14. A method of treating amblyopia in a human, comprising delivering a denervating drug to a dominant eye optic nerve, monitoring visual acuity in the amblyopic eye, and reversing denervation upon achieving a selected degree of visual acuity in a corresponding amblyopic eye.

* * * * *

UNITED STATES PATENT AND TRADEMARK OFFICE
CERTIFICATE OF CORRECTION

PATENT NO. : 6,692,481 B2 Page 1 of 1
APPLICATION NO. : 10/186062
DATED : February 17, 2004
INVENTOR(S) : Guerrero It is certified that error appears in the above-identified patent and that said Letters Patent is hereby corrected as shown below:

<u>On Title Page</u>:
Assistant Examiner should read -- Kevin C. Sirmons --.

As the claims are currently numbered:

In claim 5, at line 1 after "claim"
"1" should be deleted,
--2—should be inserted.

In claim 6, at line 1 after "claim"
"1" should be deleted,
--2—should be inserted.

Signed and Sealed this

Fifth Day of September, 2006

JON W. DUDAS
*Director of the United States Patent and Trademark Office*